US00PP19391P2

(12) United States Plant Patent
Podaras et al.

(10) Patent No.: US PP19,391 P2
(45) Date of Patent: Oct. 28, 2008

(54) ***DIERVILLA* PLANT NAMED 'LPDC PODARAS'**

(50) Latin Name: *Diervilla sessilifolia*
Varietal Denomination: LPDC Podaras

(75) Inventors: Peter Podaras, Ithaca, NY (US); Harold M. Pellett, Minnetrista, MN (US)

(73) Assignee: Landscape Plant Development Center, Mound, MN (US)

( * ) Notice: Subject to any disclaimer, the term of this patent is extended or adjusted under 35 U.S.C. 154(b) by 0 days.

(21) Appl. No.: 11/895,758

(22) Filed: Aug. 27, 2007

(51) Int. Cl.
*A01H 5/00* (2006.01)

(52) U.S. Cl. ..... Plt./226

(58) Field of Classification Search ..... Plt./226
See application file for complete search history.

*Primary Examiner*—Kent L. Bell
*Assistant Examiner*—June Hwu
(74) *Attorney, Agent, or Firm*—Penny J. Aguirre

(57) ABSTRACT

A new cultivar of *Diervilla sessilifolia,* 'LPDC Podaras', characterized by its variegated leaves with deep green centers surrounded by yellow to creamy white margins, its red stems, its cymes of yellow honeysuckle-like flowers in early summer, its hardiness to U.S.D.A Zone 4, its ease of propagation by softwood cuttings and its vigorous growth rate.

2 Drawing Sheets

Botanical classification: *Diervilla sessilifolia.*
Variety denomination: 'LPDC Podaras'.

BACKGROUND OF THE INVENTION

The present invention relates to a new and distinct cultivar of *Diervilla sessilifolia* and will be referred to hereafter by its cultivar name, 'LPDC Podaras'. 'LPDC Podaras' is a new cultivar of Southern bush honeysuckle grown for use as a landscape plant.

The inventors discovered 'LPDC Podaras' in a cultivated area in Ithaca, N.W. in 2005. The new cultivar arose as a naturally occurring branch mutation found on a plant derived from seed of unnamed plants of *Diervilla sessilifolia* in an outdoor nursery trial bed.

Asexual reproduction of the new cultivar was first accomplished by the inventors using softwood stem cuttings in 2006 in Ithaca, N.Y. The characteristics of 'LPDC Podaras' have been determined to be stable and are reproduced true to type in successive generations.

SUMMARY OF THE INVENTION

The following traits have been repeatedly observed and represent the characteristics of the new cultivar as grown outdoors in trail beds and in containers in Ithaca, N.Y. and Mound, Minn. These attributes in combination distinguish 'LPDC Podaras' as a unique cultivar of *Diervilla.*

1. 'LPDC Podaras' exhibits variegated foliage; exhibiting leaves having deep green centers surrounded by yellow to creamy white colored margins.
2. The stems of the new growth of 'LPDC Podaras' turn red as they mature.
3. 'LPDC Podaras' exhibits blooms in early summer with terminal and axillary cymes of yellow honeysuckle-like flowers.
4. 'LPDC Poaras' has a vigorous growth rate and is readily propagated by softwood cuttings.
5. 'LPDC Podaras' is hardy to U.S.D.A Zone 4.

'LPDC Podaras' is unique for its variegated foliage, a characteristic that is not found on any species or cultivars of *Diervilla* known to the inventors. 'LPDC Podaras' has similar characteristics of the parent species, *Diervilla sessilifolia,* and differs primarily in having variegated foliage. The only other known cultivar of *Diervilla sessilifolia* known to the inventors is 'Butterfly' (not patented). 'Butterfly' has dark green, non-variegated foliage that turns bronze-purple in fall.

BRIEF DESCRIPTION OF THE DRAWING

The accompanying colored photographs illustrate the overall appearance and distinct characteristics of 2 year-old plants of the new *Dievilla* as grown outdoor in 3-gallon containers in Ithaca, N.Y.

The photograph in FIG. 1 illustrates the overall appearance of 'LPDC Podaras'.

Figure 1:
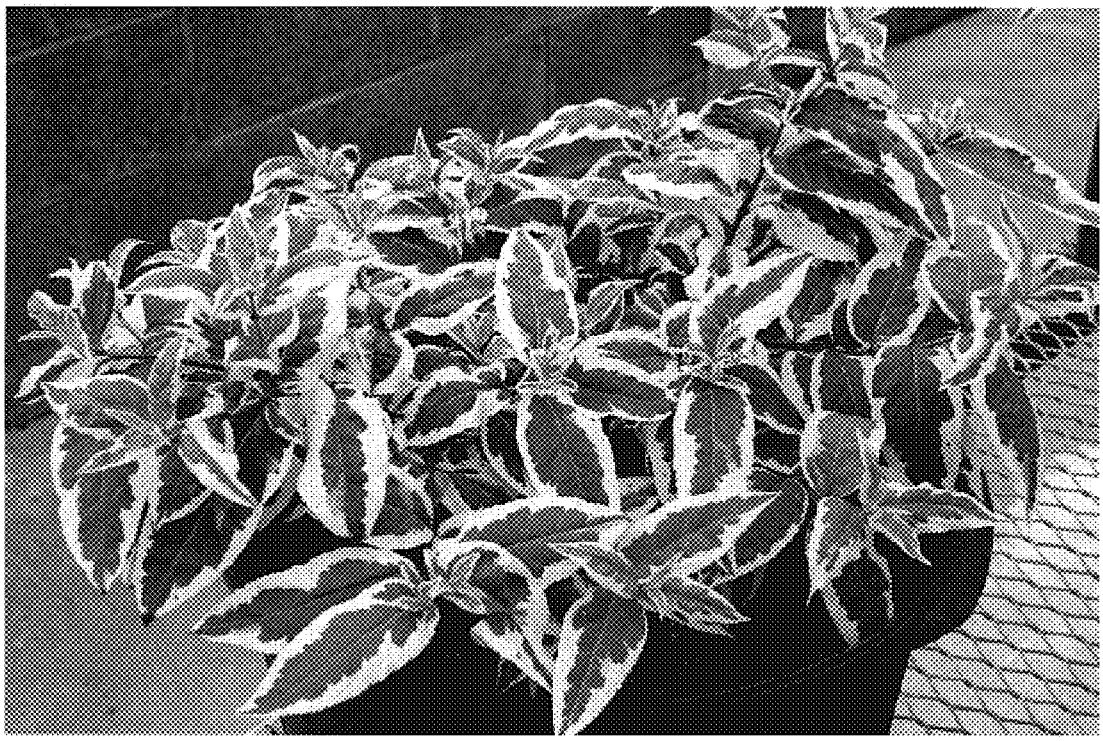
Figure 2:
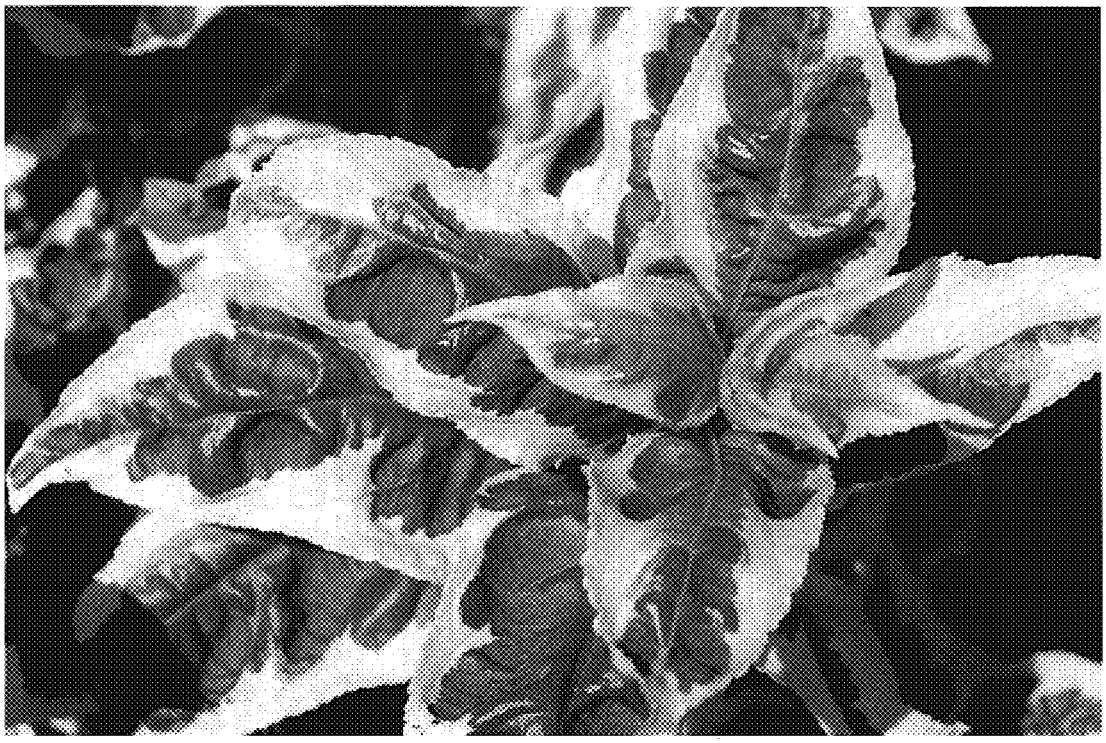

The photograph in FIG. 2 is a close-up view of the foliage and illustrates the coloration of the mature and emerging leaves of 'LPDC Podaras'.

Figure 3:
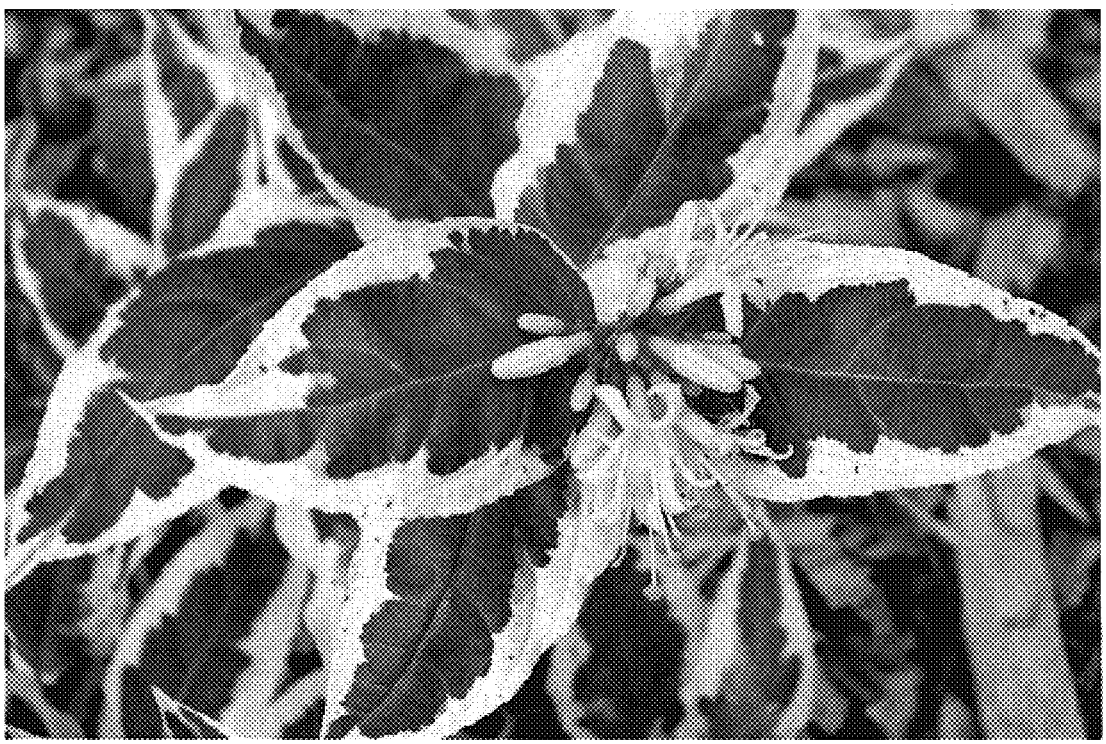

The photograph in FIG. 3 is a close-up view of an inflorescence of 'LPDC Podaras'.

The colors in the photographs are as close as possible with the digital photography techniques available, the color values cited in the detailed botanical description accurately describe the colors of the new *Diervilla.*

DETAILED BOTANICAL DESCRIPTION

The following is a detailed description of 2 year-old plants of the new cultivar as grown outdoors in 3-gallon containers in Chaska, Minn. The phenotype of the new cultivar may vary with variations in environmental, climatic, and cultural conditions, as it has not been tested under all possible environmental conditions. The color determination is in accordance with the 2001 R.H.S. Colour Chart of the Royal Horticultural Society, London, England, except where general color terms of ordinary dictionary significance are used.

General description:

*Botanical classification.*—'LPDC Podaras' is a cultivar of *Diervilla sessilifolia.*

*Parentage.*—Naturally occurring branch mutation of unnamed plants of *Diervilla sessilifolia.*

*Blooming period.*—Blooms for 2 to 3 weeks in early summer in New York and Minnesota.

*Plant habit.*—Low growing, deciduous shrub, cascading, stoloniferous.

*Culture.*—Grows well in fertile, well-drained soils and suitable for low maintenance, woodland, and hillside plantings in full sun to partial shade.

*Height and spread.*—Reaches about 1 m in height and width.

*Cold hardiness.*—U.S.D.A. Zone 4.

*Diseases resistance.*—No disease problems were observed.

*Root description.*—Fibrous and stoloniferous.

Growth and propagation:

*Propagation.*—Softwood stem cuttings.

*Root development.*—Roots develop in 10 to 14 days in summer under greenhouse conditions on a mist bench without supplemental lighting.

*Growth rate.*—Vigorous.

Stem description:

*Shape.*—Tertragonal.

*Stem color.*—New growth emerges 144C and becomes flushed with 178A as is matures, particularly on upper surface, mature wood 199C overlaid on 144C.

*Stem size.*—Main stems; about 7 cm in diameter, flowering lateral branches averages about 33 cm in length and 2.5 mm in width.

*Stem surface.*—Pubescent prior to bark formation.

*Internode length.*—Average of 2 cm.

*Branching.*—Average of 10 lateral branches on 3 gallon-container, secondary branches formed freely if pinched.

Foliage description:

*Leaf shape.*—Lanceolate.

*Leaf division.*—Simple.

*Leaf base.*—Cuneate.

*Leaf apex.*—Acuminate.

*Leaf fragrance.*—None.

*Leaf venation.*—Odd-pinnate, not prominent, midrib is conspicuous on lower surface only, 144B in color.

*Leaf margins.*—Serrulate.

*Leaf arrangement.*—Opposite.

*Leaf attachment.*—Sessile.

*Leaf surface.*—Glabrous on upper surface, finely pubescent on lower surface.

*Leaf size.*—Average of 9 cm in length and 4 cm in width when mature.

*Leaf quantity.*—Average of 12 on a branch 30 cm in length.

*Leaf variegation pattern.*—Medium to dark green centers surrounded by a yellow to creamy white colored margins, centers comprise about 2 thirds of the leaf area.

*Leaf color.*—Newly expanded leaves upper and lower surface; center 144A and margin 4C, mature leaves upper surface: center 139A and margin 8D, mature leaves lower surface: center 191A and margin 8D.

*Stipules.*—About 2 mm in length and 1 mm in width, color 8D with flush of 187A, pubescent.

*Stipules.*—Not present.

Inflorescence description:

*Inflorescence type.*—Terminal and axillary cymes of tubular flowers.

*Inflorescence size.*—About 3.5 cm in depth and width.

*Flower buds.*—Oblong in shape, 1B in color, about 1 cm in length and 3 mm in width, surface is waxy and finely pubescent.

*Flower fragrance.*—Not detectable.

*Lastingness of inflorescence.*—Cyme blooms for about 2 weeks.

*Flower quantity.*—Average of 27 flowers per terminal cyme.

*Flower type.*—Perfect, tubular.

*Flower size.*—Average of 9 mm in diameter and 1.5 cm in depth.

*Peduncles.*—About 1.4 cm in length and 1.5 mm in diameter, 144A in color, pubescent surface, round in shape.

*Pedicels.*—Up to 5 mm in length and 1 mm in diameter, 144A in color, pubescent surface, round in shape.

*Calyx.*—Comprised of short sepals arising from apex of ovary, about 4 mm in diameter and 2 mm in depth, persistent.

*Sepals.*—5, lanceolate in shape, acute apex, base fused to ovary, 145D in color, membranous and glandular surface, entire margin, about 2 mm in length and 1 mm in width at base.

*Corolla.*—Tubular but bilabiate-like in appearance with 4 petals recurved and one petal less recurved.

*Petals.*—5, lower region fused into tube with upper ⅓ spreading and recurved, unfused region is oblong-ovate in shape, upper and lower surface is membranous and waxy with hairs on upper surface, margin entire, fused base, rounded to acute apex, about 1.5 cm in length and 2 mm in width, 4B in color on both surfaces becoming speckled with 187A when mature.

Reproductive organs:

*Gynoecium.*—Pistils; 1, exserted, about 1.7 cm in length and 1 mm in width, style; very fine, 1.6 cm in length, 145C in color, stigma; globose, about 1 mm in diameter, 144A in color, ovary; inferior, 2-celled, oblong in form, 144A in color, up to 5 mm in depth and 1.5 mm in diameter.

*Androcoecium.*—Stamens; 5, exserted, about 1.5 cm in length, filaments; adnate to petals below exsertion, 145C in color, about 1.1 mm in length and 0.5 mm in width, anthers; 4B in color, dorsifixed, pollen; abundant, between 165A and 165B in color.

*Fruit and seed.*—Fruit; a slender, 2-chambered, thin-walled capsule, about 2 mm in diameter and 8 mm in length, 144A in color, seeds numerous and minute.

We claim:

1. A new and distinct cultivar of *Diervilla* plant named 'LPDC Podaras' as herein illustrated and described.

* * * * *